(12) United States Patent
Heikenfeld et al.

(10) Patent No.: US 10,182,795 B2
(45) Date of Patent: Jan. 22, 2019

(54) DEVICES FOR INTEGRATED, REPEATED, PROLONGED, AND/OR RELIABLE SWEAT STIMULATION AND BIOSENSING

(71) Applicant: University Of Cincinnati, Cincinnati, OH (US)

(72) Inventors: Jason C. Heikenfeld, Cincinnati, OH (US); Zachary Cole Sonner, Cincinnati, OH (US)

(73) Assignee: University Of Cincinnati, Cincinnati, OH (US)

( * ) Notice: Subject to any disclaimer, the term of this patent is extended or adjusted under 35 U.S.C. 154(b) by 1033 days.

(21) Appl. No.: 14/516,962

(22) Filed: Oct. 17, 2014

(65) Prior Publication Data

US 2015/0112164 A1 Apr. 23, 2015

Related U.S. Application Data

(60) Provisional application No. 61/892,859, filed on Oct. 18, 2013, provisional application No. 62/003,707, filed on May 28, 2014.

(51) Int. Cl.
*A61B 5/05* (2006.01)
*A61B 10/00* (2006.01)
(Continued)

(52) U.S. Cl.
CPC ........ *A61B 10/0064* (2013.01); *A61B 5/0531* (2013.01); *A61B 5/0537* (2013.01);
(Continued)

(58) Field of Classification Search
CPC ........... A61B 10/00; A61B 5/00; A61B 5/053; A61B 5/1491; A61B 5/0537;
(Continued)

(56) References Cited

U.S. PATENT DOCUMENTS

| 4,190,060 A | 2/1980 | Greenleaf et al. |
| 4,542,751 A | 9/1985 | Webster et al. |

(Continued)

FOREIGN PATENT DOCUMENTS

| CA | 2869469 A1 | 10/2013 |
| CN | 1874720 A | 12/2006 |

(Continued)

OTHER PUBLICATIONS

International Searching Authority, Search Report and Written Opinion issued in International Application No. PCT/US2015/032866 dated Nov. 19, 2015, 12 pages.

(Continued)

*Primary Examiner* — Navin Natnithithadha
*Assistant Examiner* — Eric Messersmith
(74) *Attorney, Agent, or Firm* — Wood Herron & Evans LLP

(57) ABSTRACT

A sweat sensing device includes a plurality of sweat collection pads communicating with a sensor. Each of the pads is activated by a timing circuit which allows one or more of the pads to be activated at a selected time and subsequent deactivated after a defined period of time. This allows for selective collection of sweat from a plurality of pads over a prolonged period of time. An impedance measuring circuit can be employed to determine if one or more of the pads becomes disconnected, in order to avoid irritation. Further, the devices can use a common microfluidic device which both transports sweat activating substance, such as pilocarpine, to the surface of the skin and directs sweat away from the skin to a sensing device.

13 Claims, 4 Drawing Sheets

(51) Int. Cl.
  *A61B 5/053* (2006.01)
  *A61B 5/1491* (2006.01)
  *A61B 5/00* (2006.01)
  *A61N 1/32* (2006.01)
  *A61B 5/145* (2006.01)
  *A61B 5/0408* (2006.01)

(52) U.S. Cl.
  CPC ........ *A61B 5/1491* (2013.01); *A61B 5/14521* (2013.01); *A61B 5/4266* (2013.01); *A61B 5/6843* (2013.01); *A61N 1/325* (2013.01); *A61B 5/04085* (2013.01); *A61B 2010/0009* (2013.01); *A61B 2562/168* (2013.01); *A61M 2202/092* (2013.01)

(58) Field of Classification Search
  CPC . A61B 5/4266; A61B 5/6843; A61B 10/0064; A61B 5/0531; A61B 5/14521; A61B 5/04085; A61B 2562/168; A61B 2010/00; A61B 2010/0009; A61N 1/32; A61N 1/325; A61M 2202/092
  See application file for complete search history.

(56) References Cited

U.S. PATENT DOCUMENTS

| | | |
|---|---|---|
| 4,756,314 A | 7/1988 | Eckenhoff et al. |
| 4,820,263 A | 4/1989 | Spevak et al. |
| 5,036,861 A | 8/1991 | Sembrowich et al. |
| 5,050,604 A | 9/1991 | Reshef et al. |
| 5,140,985 A | 8/1992 | Schroeder et al. |
| 5,246,003 A | 9/1993 | DeLonzor |
| 5,438,984 A | 8/1995 | Schoendorfer |
| 5,556,789 A | 9/1996 | Goerlach-Graw et al. |
| 5,814,599 A | 9/1998 | Mitragotri et al. |
| 5,944,662 A | 8/1999 | Schoendorfer |
| 6,198,953 B1 | 3/2001 | Webster et al. |
| 6,256,533 B1 | 7/2001 | Yuzhakov et al. |
| 6,269,265 B1 | 7/2001 | Anderson |
| 6,299,578 B1 | 10/2001 | Kurnik et al. |
| 6,592,529 B2 | 7/2003 | Marett |
| 6,666,821 B2 * | 12/2003 | Keimel ............ A61B 5/14865 600/345 |
| 7,190,986 B1 | 3/2007 | Hannula et al. |
| 7,219,534 B2 | 5/2007 | Campbell |
| 7,378,054 B2 | 5/2008 | Karmali |
| 7,383,072 B2 | 6/2008 | Edmonson et al. |
| 7,384,396 B2 | 6/2008 | Samuels et al. |
| 7,749,445 B2 | 7/2010 | Masters |
| 7,813,780 B2 | 10/2010 | Shah et al. |
| 7,842,234 B2 | 11/2010 | Lauks et al. |
| 7,959,791 B2 | 6/2011 | Kjaer et al. |
| 8,125,539 B2 | 2/2012 | Takashima |
| 8,128,889 B2 | 3/2012 | Fujimoto et al. |
| 8,252,248 B2 | 8/2012 | Kramer |
| 8,391,946 B2 | 3/2013 | Sugenoya et al. |
| 8,593,287 B2 | 11/2013 | Hayter et al. |
| 8,617,067 B2 | 12/2013 | Jain et al. |
| 9,133,024 B2 | 9/2015 | Phan et al. |
| 2002/0091312 A1 | 7/2002 | Berner et al. |
| 2003/0135100 A1 | 7/2003 | Kim et al. |
| 2003/0191376 A1 | 10/2003 | Samuels et al. |
| 2003/0201194 A1 | 10/2003 | Heller et al. |
| 2004/0249310 A1 | 12/2004 | Shartle et al. |
| 2004/0267189 A1 | 12/2004 | Mavor et al. |
| 2005/0069925 A1 | 3/2005 | Ford et al. |
| 2005/0106713 A1 | 5/2005 | Phan et al. |
| 2005/0177035 A1 | 8/2005 | Botvinick et al. |
| 2005/0192520 A1 | 9/2005 | Tapper |
| 2005/0197554 A1 | 9/2005 | Polcha |
| 2006/0004271 A1 | 1/2006 | Peyser et al. |
| 2006/0062852 A1 | 3/2006 | Holmes |
| 2006/0127964 A1 | 6/2006 | Ford et al. |
| 2006/0253011 A1 | 11/2006 | Edmonson et al. |
| 2006/0254341 A1 | 11/2006 | Campbell |
| 2007/0027383 A1 | 2/2007 | Peyser et al. |
| 2007/0032731 A1 | 2/2007 | Lovejoy et al. |
| 2007/0179371 A1 | 8/2007 | Peyser et al. |
| 2008/0015494 A1 * | 1/2008 | Santini, Jr. .......... A61M 5/1409 604/65 |
| 2008/0045816 A1 | 2/2008 | Jang et al. |
| 2008/0154179 A1 | 6/2008 | Cantor et al. |
| 2008/0286349 A1 | 11/2008 | Nomoto et al. |
| 2008/0306362 A1 | 12/2008 | Davis |
| 2009/0270704 A1 | 10/2009 | Peyser et al. |
| 2010/0044224 A1 | 2/2010 | Kataky |
| 2010/0063372 A1 | 3/2010 | Potts et al. |
| 2010/0130843 A1 | 5/2010 | Caceres Galvez et al. |
| 2010/0132485 A1 | 6/2010 | Erez et al. |
| 2010/0179403 A1 | 7/2010 | Martinsen et al. |
| 2010/0198521 A1 | 8/2010 | Haick |
| 2011/0079521 A1 | 4/2011 | Revol-Cavalier |
| 2011/0118656 A1 | 5/2011 | Eckhoff et al. |
| 2011/0178380 A1 | 7/2011 | Chowdhury |
| 2011/0196283 A1 | 8/2011 | Imran et al. |
| 2011/0208458 A1 | 8/2011 | Pinter et al. |
| 2011/0275918 A1 * | 11/2011 | Yamashita .......... A61B 5/14521 600/345 |
| 2012/0004570 A1 | 1/2012 | Shimizu et al. |
| 2012/0028283 A1 | 2/2012 | Ross et al. |
| 2012/0123220 A1 | 5/2012 | Iyer et al. |
| 2012/0165626 A1 | 6/2012 | Irina et al. |
| 2012/0209226 A1 | 8/2012 | Simmons et al. |
| 2012/0229661 A1 | 9/2012 | Sekiguchi et al. |
| 2012/0277697 A1 | 11/2012 | Haghgooie et al. |
| 2012/0285829 A1 | 11/2012 | Mount et al. |
| 2012/0317430 A1 | 12/2012 | Rahman et al. |
| 2012/0323097 A9 | 12/2012 | Chowdhury |
| 2013/0006079 A1 | 1/2013 | Feldman et al. |
| 2013/0010108 A1 | 1/2013 | Hashizume et al. |
| 2013/0013028 A1 | 1/2013 | Kriksunov et al. |
| 2013/0053668 A1 | 2/2013 | Lin |
| 2013/0079605 A1 | 3/2013 | Bandaru et al. |
| 2013/0099937 A1 | 4/2013 | Azimi |
| 2013/0108667 A1 | 5/2013 | Soikum et al. |
| 2013/0123595 A1 * | 5/2013 | Currie ............... A61B 5/14532 600/347 |
| 2013/0183399 A1 | 7/2013 | Blow et al. |
| 2013/0245388 A1 | 9/2013 | Rafferty et al. |
| 2013/0306491 A1 | 11/2013 | Briman et al. |
| 2013/0317333 A1 | 11/2013 | Yang et al. |
| 2014/0012114 A1 | 1/2014 | Zevenbergen et al. |
| 2014/0025000 A1 | 1/2014 | Currie et al. |
| 2014/0206977 A1 | 7/2014 | Bahney et al. |
| 2014/0275862 A1 | 9/2014 | Kennedy |
| 2014/0276220 A1 | 9/2014 | Briscoe et al. |
| 2014/0343371 A1 | 11/2014 | Sowers, II et al. |
| 2015/0057515 A1 | 2/2015 | Hagen et al. |
| 2015/0112164 A1 | 4/2015 | Heikenfeld et al. |
| 2015/0112165 A1 | 4/2015 | Heikenfeld |
| 2016/0058354 A1 | 3/2016 | Phan et al. |
| 2016/0066828 A1 | 3/2016 | Phan et al. |
| 2016/0157768 A1 | 6/2016 | Braig et al. |

FOREIGN PATENT DOCUMENTS

| | | |
|---|---|---|
| CN | 1969184 A | 5/2007 |
| CN | 1984716 A | 6/2007 |
| CN | 101489470 A | 7/2009 |
| EP | 0282349 A2 | 9/1988 |
| EP | 0453283 A1 | 10/1991 |
| EP | 0634215 A1 | 1/1995 |
| EP | 1500937 A1 | 1/2005 |
| EP | 1637889 A1 | 3/2006 |
| EP | 2551784 A1 | 1/2013 |
| JP | H07-77525 A | 3/1995 |
| JP | H08-504513 A | 5/1996 |
| JP | 2007503958 A | 3/2007 |
| JP | 2007532260 A | 11/2007 |
| JP | 2008505330 A | 2/2008 |
| JP | 200963597 A | 3/2009 |
| JP | 2009118420 A | 5/2009 |
| WO | 9011519 A1 | 10/1990 |

(56) References Cited

FOREIGN PATENT DOCUMENTS

| | | | |
|---|---|---|---|
| WO | 9414062 | A1 | 6/1994 |
| WO | 0014535 | A1 | 3/2000 |
| WO | 01/88525 | A1 | 11/2001 |
| WO | 2006133101 | A2 | 12/2006 |
| WO | 2007097754 | A1 | 8/2007 |
| WO | 2007146047 | A1 | 12/2007 |
| WO | 2008083687 | A1 | 7/2008 |
| WO | 2008095940 | A1 | 8/2008 |
| WO | 2009004001 | A1 | 1/2009 |
| WO | 2009052321 | A2 | 4/2009 |
| WO | 2010/017578 | A1 | 2/2010 |
| WO | 2011117952 | A1 | 9/2011 |
| WO | 2013152087 | A2 | 10/2013 |
| WO | 2013181436 | A1 | 12/2013 |
| WO | 2014001577 | A1 | 1/2014 |
| WO | 2014025430 | A2 | 2/2014 |
| WO | 2015184072 | A1 | 12/2015 |
| WO | 2015184097 | A2 | 12/2015 |
| WO | 2016049019 | A1 | 3/2016 |
| WO | 2016061362 | A2 | 4/2016 |
| WO | 2016/090189 | A1 | 6/2016 |

OTHER PUBLICATIONS

International Searching Authority, Search Report and Written Opinion issued in International Application No. PCT/US2015/032893 dated Nov. 13, 2015, 14 pages.

International Searching Authority, Search Report and Written Opinion issued in International Application No. PCT/US2015/040113 dated Feb. 4, 2016, 14 pages.

International Searching Authority, Search Report and Written Opinion issued in International Application No. PCT/US2015/051439 dated Dec. 28, 2015, 7 pages.

International Searching Authority, Invitation to Pay Additional Search Fees and, Where Applicable, Protest Fee, and Communication Relating to the Results of the Partial International Search, issued in International Application No. PCT/US2015/032843 dated Aug. 18, 2015, 2 pages.

International Searching Authority, Invitation to Pay Additional Search Fees and, Where Applicable, Protest Fee, and Communication Relating to the Results of the Partial International Search, issued in International Application No. PCT/US2015/040113 dated Dec. 1, 2015, 2 pages.

International Searching Authority, Invitation to Pay Additional Search Fees and, Where Applicable, Protest Fee, and Communication Relating to the Results of the Partial International Search, issued in International Application No. PCT/US2015/032866 dated Aug. 31, 2015, 2 pages.

International Searching Authority, Invitation to Pay Additional Search Fees and, Where Applicable, Protest Fee, and Communication Relating to the Results of the Partial International Search, issued in International Application No. PCT/US2015/032893 dated Aug. 31, 2015, 2 pages.

International Searching Authority, Search Report and Written Opinion issued in International Application No. PCT/US16/18635 dated May 6, 2016, 12 pages.

International Searching Authority, Search Report and Written Opinion issued in International Application No. PCT/US16/17726 dated May 12, 2016, 9 pages.

International Bureau, Notification Concerning Transmittal of International Preliminary Report on Patentability issued in International Application No. PCT/US13/35092, 14 pages.

International Searching Authority, Invitation to Pay Additional Fees and, Where Applicable, Protest Fee, and Communication Relating to the Results of the Partial International Search, issued in International Application No. PCT/US13/35092, 9 pages.

Fu et al., "Controlled Reagent Transport in Disposable 2D Paper Networks", The Royal Society of Chemistry 2010, Lab Chip, 2010, 10, 918-920.

Chinese Patent Office, First Office Action issued in Chinese Application No. 201380028053.8 dated Dec. 21, 2015, 4 pages.

International Searching Authority, Search Report and Written Opinion issued in International Application No. PCT/US16/59392 dated Oct. 28, 2016, 13 pages.

International Searching Authority, Search Report and Written Opinion issued in International Application No. PCT/US16/43862 dated Oct. 19, 2016, 14 pages.

International Searching Authority, Search Report and Written Opinion issued in International Application No. PCT/US16/50928 dated Sep. 9, 2016, 8 pages.

Australian Patent Office, Patent Examination Report No. 1 issued in Australian Application No. 2013243541 dated Nov. 25, 2016, 4 pages.

European Patent Office, Written Opinion of the International Search Authority / International Preliminary Report on Patentability for PCT/US2013/035092 dated Oct. 16, 2014 (14 pages).

European Patent Office, Partial European Search Report issued in European Application No. 16203346.8-1657 dated Mar. 24, 2017, 7 pages.

Japanese Patent Office, Office Action issued in Japanese Application No. 2015-504702 dated Jan. 20, 2017, 7 pages (including English language translation).

Stoppa, Matteo, et. al., "Wearable Electronics and Smart Tectiles: A Critical Review," Sensors, 2014, pp. 11957-11992, vol. 14 (36 pages).

Australian Patent Office, Notice of Acceptance for Patent Application issued in Australian Application No. 2013243541 dated Mar. 23, 2017 (3 pages).

Chinese Patent Office, Third Office Action issued in Chinese Application No. 201380028053.8 dated Mar. 20, 2017, 17 pages (including English language translation).

Chinese Patent Office, Second Office Action issued in Chinese Application No. 201380028053.8 dated Sep. 20, 2016, 8 pages (including English language translation).

International Searching Authority, Search Report and Written Opinion issued in International Application No. PCT/US2017/013453 dated May 18, 2017, 14 pages.

International Searching Authority, Search Report and Written Opinion issued in International Application No. PCT/US2017/039421 dated Sep. 6, 2017, 10 pages.

International Searching Authority, Search Report and Written Opinion issued in International Application No. PCT/US2017/040588 dated Sep. 25, 2017, 11 pages.

International Searching Authority, Search Report and Written Opinion issued in corresponding International Application No. PCT/US2014/061083 dated Mar. 31, 2015, 18 pages.

International Searching Authority, Search Report and Written Opinion issued in corresponding International Application No. PCT/US2014/061098 dated Dec. 12, 2014, 13 pages.

International Searching Authority, Invitation to Pay Additional Search Fees and, Where Applicable, Protest Fee, and Communication Relating to the Results of the Partial International Search, issued in corresponding International Application No. PCT/US2014/061083 dated Dec. 15, 2014, 6 pages.

International Searching Authority, Search Report and Written Opinion issued in corresponding International Application No. PCT/US2015/032830 dated Aug. 14, 2015, 9 pages.

International Searching Authority, Search Report and Written Opinion issued in corresponding International Application No. PCT/US2015/032843 dated Oct. 26, 2015, 11 pages.

European Patent Office, Supplemental European Search Report issued in European Application No. 15799514.3-1657 dated Dec. 7, 2017, 8 pages.

European Patent Office, Supplemental European Search Report issued in European Application No. 15799317.1-1657 dated Dec. 21, 2017, 9 pages.

European Patent Office, Partial European Search Report issued in European Application No. 15800043.0-115 dated Jan. 8, 2018, 13 pages.

International Searching Authority, Search Report and Written Opinion issued in International Application No. PCT/US2017/047574 dated Nov. 16, 2017, 14 pages.

(56) References Cited

OTHER PUBLICATIONS

International Searching Authority, Search Report and Written Opinion issued in International Application No. PCT/US2017/052651 dated Dec. 12, 2017, 14 pages.

Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.

Sonner, Z., et al., "The microfluidics of the eccrine sweat gland, including biomarker partitioning, transport, and biosensing implications," Biomicrofluidics, vol. 9, pp. 031301-1-031301-19, CrossMark, 19 pages.

European Patent Office, Official Communication for EP Application No. 13 718 933.8-1101 dated Feb. 14, 2018 (5 pages).

European Patent Office, Extended European Search Report issued in European Application No. 15819306.0-1115 dated Feb. 9, 2018 (9 pages).

International Searching Authority, Search Report and Written Opinion issued in International Application No. PCT/US2017/067495 dated Mar. 1, 2018, 10 pages.

International Searching Authority/US, International Search Report and Written Opinion issued in corresponding PCT Application No. PCT/US2016/059392, dated Feb. 15, 2017 (12 pages).

European Patent Office, Extended Search Report issued in European Application No. 15844313.5 dated Mar. 15, 2018, 15 pages.

De Jong, J. et al., "Membranes and microfluidics: a review," Lab Chip, 2006, 6, 1125-1139 (15 pages).

Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.

European Patent Office, Extended European Search Report issued for European Patent Application No. 15800043.0, dated Apr. 16, 2018, 11 pages.

* cited by examiner

DEVICES FOR INTEGRATED, REPEATED, PROLONGED, AND/OR RELIABLE SWEAT STIMULATION AND BIOSENSING

CROSS-REFERENCE TO RELATED APPLICATIONS

This application claims the benefit of U.S. Provisional Applications No. 61/892,859, entitled "SWEAT STIMULATION FOR INTEGRATED OR REPEATED BIOSENSING" filed Oct. 18, 2013, and 62/003,707 entitled "DEVICE CONSTRUCTION FOR PROLONGED AND RELIABLE SWEAT STIMULATION AND SENSING" filed May 28, 2014, the disclosures of which are hereby incorporated by reference herein in their entirety. The disclosure of PCT/US13/35092, filed Apr. 3, 2013 is also incorporated herein by reference in its entirety.

STATEMENT REGARDING FEDERALLY SPONSORED RESEARCH OR DEVELOPMENT

The present invention was made, at least in part, with support from the U.S. Government and funds identified as SAPGrant No. 1008512, awarded by the U.S. Air Force Research Labs. The U.S. Government has certain rights in the present invention.

BACKGROUND OF THE INVENTION

Sweat sensing technologies have enormous potential for applications ranging from athletics, to neonates, to pharmacological monitoring, to personal digital health, to name a few applications. This is because sweat contains many of the same biomarkers, chemicals, or solutes that are carried in blood, which can provide significant information which enables one to diagnose ailments, health status, toxins, performance, and other physiological attributes even in advance of any physical sign. Furthermore sweat itself, and the action of sweating, or other parameters, attributes, solutes, or features on or near skin or beneath the skin, can be measured to further reveal physiological information.

Sweat has significant potential as a sensing paradigm, but it has not emerged beyond decades-old usage in infant chloride assays for Cystic Fibrosis (e.g. Wescor Macroduct system) or in illicit drug monitoring patches (e.g. Pharm-Check drugs of abuse patch by PharmChem). The majority of medical literature discloses slow and inconvenient sweat stimulation and collection, transport of the sample to a lab, and then analysis of the sample by a bench-top machine and a trained expert. All of this is so labor intensive, complicated, and costly, that in most cases, one would just as well implement a blood draw since it is the gold standard for most forms of high performance biomarker sensing. Hence, sweat sensing has not achieved its fullest potential for biosensing, especially for continuous or repeated biosensing or monitoring. Furthermore, attempts at using sweat to sense 'holy grails' such as glucose have failed to produce viable commercial products, reducing the publically perceived capability and opportunity space for sweat sensing. A similar conclusion has been made very recently in a substantial 2014 review provided by Castro titled "Sweat: A sample with limited present applications and promising future in metabolomics", which states: "The main limitations of sweat as clinical sample are the difficulty to produce enough sweat for analysis, sample evaporation, lack of appropriate sampling devices, need for a trained staff, and errors in the results owing to the presence of pilocarpine. In dealing with quantitative measurements, the main drawback is normalization of the sampled volume."

Many of these drawbacks stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sweat sensing technology into intimate proximity with sweat as it is generated. Sweat sensing therefore becomes a compelling new paradigm that clearly was overlooked in terms of its ultimate potential as a biosensing platform.

Sweat sensors have many potential advantages over other biofluid sensors. But one potentially confounding factor is that prolonged stimulation of sweat can be problematic as some individuals can be hyper sensitive to prolonged stimulation of sweat or their glands will adapt to sweat stimulation and provide no or reduced response to sweat stimulation by heat, electricity, iontophoresis, or other means. Furthermore, for prolonged stimulation, risk of electrode detachment is a risk, and can even be a risk at the onset of stimulation. Solutions for solving these risks are lacking.

The number of active sweat glands varies greatly among different people, though comparisons between different areas (ex. axillae versus groin) show the same directional changes (certain areas always have more active sweat glands while others always have fewer). The palm is estimated to have around 370 sweat glands per $cm^2$; the back of the hand 200 per $cm^2$; the forehead 175 per $cm^2$; the breast, abdomen, and forearm 155 per $cm^2$; and the back and legs 60-80 per $cm^2$. Assuming use of a sweat gland density of 100/$cm^2$, a sensor that is 0.55 cm in radius (1.1 cm in diameter) would cover ~1 $cm^2$ area or approximately 100 sweat glands. According to "Dermatology: an illustrated color text" 5th edition, the human body excretes a minimum of 0.5 liter per day of sweat, and has 2.5 million sweat glands on average and there are 1440 minutes per day. For prepubescent children, these sweat volumes are typically lower. For 2.5 million glands that rate is 0.2 µl per gland per day or 0.14 nL/min/gland. This is the minimum 'average' sweat rate generated per pore, on average, with some possible exceptions being where sweating increases slightly on its own (such as measuring sleep cycles, etc.). Again, from "Dermatology: an illustrated color text" 5th edition, the maximum sweat generated per person per day is 10 liters which on average is 4 µL per gland maximum per day, or about 3 nL/min/gland. This is about 20× higher than the minimum rate.

According to Buono 1992, J. Derm. Sci. 4, 33-37, "Cholinergic sensitivity of the eccrine sweat gland in trained and untrained men", the maximum sweat rates generated by pilocarpine stimulation are about 4 nL/min/gland for untrained men and 8 nL/min/gland for trained (exercising often) men. Other sources indicate maximum sweat rates of an adult can be up to 2-4 liters per hour or 10-14 liters per day (10-15 g/min·$m^2$), which based on the per hour number translates to 20 nL/min/gland or 3 nL/min/gland. Sweat stimulation data from "Pharmacologic responsiveness of isolated single eccrine sweat glands" by K. Sato and F. Sato (the data was for extracted and isolated monkey sweat glands, which are very similar to human ones), suggests a rate up to ~5 nL/min/gland is possible with stimulation, and several types of sweat stimulating substances are disclosed. For simplicity, we can conclude that the minimum sweat on average is ~0.1 nL/min/gland and the maximum is ~5 nL/min/gland, which is about a 50× difference between the two.

Based on the assumption of a sweat gland density of 100/cm², a sensor that is 0.55 cm in radius (1.1 cm in diameter) would cover ~1 cm² area or approximately 100 sweat glands. Assuming a dead volume under each sensor of 50 μm height or 50×10⁻⁴ cm, and that same 1 cm² area, provides a volume of 50E-4 cm³ or about 50E-4 mL or 5 μL of volume. With the maximum rate of 5 nL/min/gland and 100 glands it would require 10 minutes to fully refresh the dead volume. With the minimum rate of 0.1 nL/min/gland and 100 glands it would require 500 minutes or 8 hours to fully refresh the dead volume. If the dead volume could be reduced by 10× to 5 μm roughly, the max and min times would be 1 minute and 1 hour, roughly respectively, but the min rate would be subject to diffusion and other contamination issues (and 5 μm dead volume height could be technically challenging). Consider the fluidic component between a sensor and the skin to be a 25 μm thick piece of paper or glass fiber with, which at 1 cm² equates to a volume of 2.5 μL of volume and if the paper was 50% porous (50% solids) then the dead volume would be 1.25 μL. With the maximum rate of 5 nL/min/gland and 100 glands it would require 2.5 minutes to fully refresh the dead volume. With the minimum rate of 0.1 nL/min/gland and 100 glands it would require ~100 minutes or ~2 hours to fully refresh the dead volume.

Sweat stimulation is commonly known to be achieved by one of several means. Sweat activation has been promoted by simple thermal stimulation, by intradermal injection of drugs such as methylcholine or pilocarpine, and by dermal introduction of such drugs using iontophoresis. Gibson and Cooke's device for iontophoresis, one of the most employed devices, provides DC current and uses large lead electrodes lined with porous material. The positive pole is dampened with 2% pilocarpine hydrochloride, and the negative one with 0.9% NaCl solution. Sweat can also be generated by orally administering a drug. Sweat can also be controlled or created by asking the subject using the patch to enact or increase activities or conditions which cause them to sweat.

Sweat rate can also be measured real time in several ways. Sodium can be utilized to measure sweat rate real time (higher sweat rate, higher concentration), as it is excreted by the sweat gland during sweating. Chloride can be utilized to measure sweat rate (higher sweat rate, higher concentration), as it is excreted by the sweat gland during sweating. Both sodium and chloride can be measured using ion-selective electrodes or sealed reference electrodes, for example placed in the sweat sensor itself and measured real time as sweat emerges onto the skin. Sato 1989, pg. 551 provides details on sweat rate vs. concentration of sodium & chloride. Electrical impedance can also be utilized to measure sweat rate. Grimnes 2011 and Tronstad 2013 demonstrate impedance and sweat rate correlations. Impedance and Na concentration, and or other measurements can be made and used to calculate at least roughly the sweat pore density and sweat flow rate from individual sweat glands, and coupled with sweat sensing or collection area to determine an overall sweat flow rate to a sensor. More indirect measurements of sweat rate are also possible through common electronic/optical/chemical measurements, including those such as pulse, pulse-oxygenation, respiration, heart rate variability, activity level, and 3-axis accelerometry, or other common readings published by Fitbit, Nike Fuel, Zephyr Technology, and others in the current wearables space, or demonstrated previously in the prior art.

With reference to FIG. 1A, a prior art sweat stimulation and sensing device 10 is positioned on skin 12 and is provided with features shown relevant to the present invention. The device 10 is adhered to the skin 12 with an adhesive 14 which carries a substrate 13, control electronics 16, at least one sensor 18, a microfluidic component 20, a reservoir or gel with pilocarpine referred to as pilocarpine source 22, an iontophoresis electrode 24, and counter electrode 26. The electrodes 24 and 26 are electrically conductive with and through the skin 12 by virtue of the conductance of materials 22, 20 and 14 and, in some cases adhesive 14 can be locally removed beneath one or more electrodes or sensors to improve conductance with the skin and/or to improve collection or interface with sweat. Adhesives can be functional as tacky hydrogels as well which promote robust electrical, fluidic, and iontophoretic contact with skin (as commercially available examples such as those by SkinTact for ECG electrodes). With reference to FIG. 1B, a top view of connections to the electronics 16 is shown, such connections by example only and not representing a limiting configuration. The electronics 16 can be a simple as a controlled current source and sensing electronics only, or more complex including computing, communication, a battery, or other features. Again, in some embodiments, the electronics may be much simpler or not needed at all.

With further reference to FIGS. 1A and 1B, if the device 10 were to stimulate sweat by virtue of iontophoretically driving a stimulating drug such as pilocarpine from the source 22 into the skin 12, it could conventionally do so for several minutes and stimulate sweat that could be collected for 10-30 minutes by the microfluidic component 20 and flow over the sensor 18 which could detect one or more solutes of interest in the sweat. This conventional stimulation and collection time frame is typical and similar to that broadly used for infant-chloride assays for cystic fibrosis testing, such as found in products by Wescor Corporation. Sweat sensors have advantages over other biofluid sensors, but one potentially confounding factor is that prolonged stimulation of sweat for more than 30 minutes could be problematic as some individuals can be hyper sensitive to prolonged stimulation of sweat or their glands, or will adapt to sweat stimulation and provide no or reduced response to sweat stimulation by heat, electricity, iontophoresis, or other means. Furthermore, for prolonged stimulation, electrode detachment can be a risk, or even be a risk at the onset of stimulation. Solutions for solving these risks are lacking. Furthermore, the stimulation can interfere with the quality of the sensing, and therefore needs to be resolved as well.

SUMMARY OF THE INVENTION

The present invention is premised on the realization that sweat can be effectively simulated and analyzed in a single, continuous, or repeated manner inside the same device. The present invention addresses the confounding factors that result in performance being too poor for many practical uses. Specifically, the present invention provides: sweat sampling and stimulation with at least one shared microfluidic component; sweat sampling and stimulation with at least one component or membrane added to mitigate the interference of a sweat stimulating portion of device with the purity of sweat delivery to the sampling portion of the device; multiple stimulation pads and some with their own sensors; timed pulsing of stimulation in some cases allowing areas of skin to rest; detection of a faulty stimulation contact with skin; and parametric specification of pads small enough to reduce irritation during sweat stimulation; and additional alternate embodiments as will be taught in the specifications.

Further, minimizing dead volume, that is the volume of sweat that must be generated to be detected by an electrode or other type of sensor, can in some cases ease some of the challenges of sweat stimulation. For example, consider a polymer matrix that is porous to sweat with 10% open porosity, and which is tacky and gel like (so it adheres and bonds to skin). If this were 50 μm thick, then the equivalent dead volume would be that of a 5 μm thick dead volume, the max and min times would be 1 minute and 1 hour, roughly respectively, and this is much less technically challenging than a highly open/porous dead volume. Reducing dead volume, isolating sweat pores, minimizing irritation, and other aspects are all desirable for prolonged stimulation of sweat for chronological monitoring applications. If dead volumes are reduced enough, hourly or even once a day readings are highly possible without need for high sweat rates.

BRIEF DESCRIPTION OF THE DRAWINGS

The objects and advantages of the present invention will be further appreciated in light of the following detailed descriptions and drawings in which.

DETAILED DESCRIPTION OF THE INVENTION

Figure 1A:
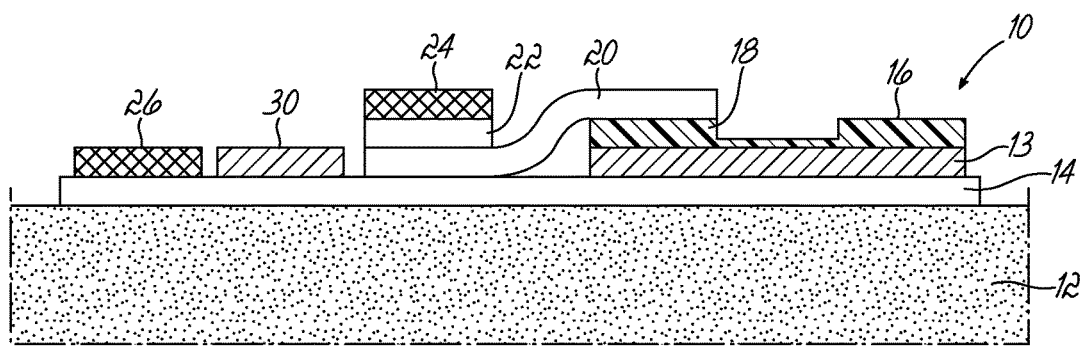
FIGS. 1A and 1B are side view and top-view diagrams of prior art.
Figure 1B:
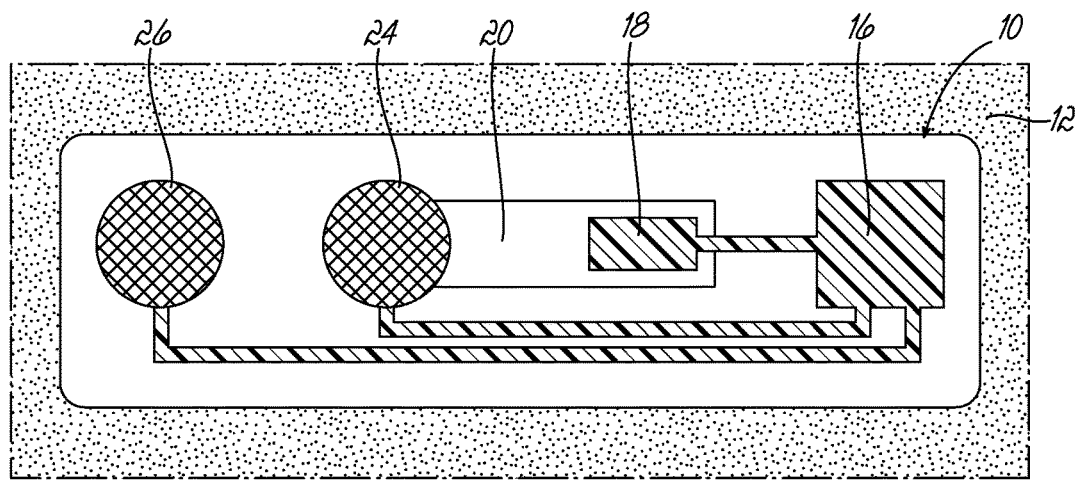

The detailed description of the present invention will be primarily be, but not entirely be, limited to subcomponents, subsystems, sub methods, of wearable sensing devices, including devices dedicated to sweat sensing. Therefore, although not described in detail here, other essential features which are readily interpreted from or incorporated with the present invention shall be included as part of the present invention. The specification for the present invention will provides specific examples to portray inventive steps, but which will not necessarily cover all possible embodiments commonly known to those skilled in the art. For example, the specific invention will not necessarily include all obvious features needed for operation, examples being a battery or power source which is required to power electronics, or for example, an wax paper backing that is removed prior to applying an adhesive patch, or for example, a particular antenna design, that allows wireless communication with a particular external computing and information display device. Several specific, but non-limiting, examples can be provided as follows. The invention includes reference to PCT/US2013/035092, the disclosure of which is included herein by reference. The present invention applies to any type of sweat sensor device. The present invention applies to sweat sensing devices which can take on forms including patches, bands, straps, portions of clothing, wearables, or any mechanism suitable to affordably, conveniently, effectively, intelligently, or reliably bring sweat stimulating, sweat collecting, and/or sweat sensing technology into intimate proximity with sweat as it is generated. In some embodiments of the present invention the device will require adhesives to the skin, but devices could also be held by other mechanisms that hold the device secure against the skin such as strap or embedding in a helmet. The present invention may benefit from chemicals, materials, sensors, electronics, microfluidics, algorithms, computing, software, systems, and other features or designs, as commonly known to those skilled in the art of electronics, biosensors, patches, diagnostics, clinical tools, wearable sensors, computing, and product design. The present invention applies to any type of device that measures sweat or sweat rate, its solutes, solutes that transfer into sweat from skin, a property of or things on the surface of skin, or measures properties or things beneath the skin.

The present invention includes all direct or indirect mechanisms or combinations of sweat stimulation, including but not limited to sweat stimulation by heat, pressure, electricity, iontophoresis or diffusion of chemical sweat stimulants, orally or injected drug that stimulate sweat, stimuli external to the body, natural bioactivity, cognitive activity, or physical activity. Any suitable technique for measuring sweat rate should be included in the present invention where measurement of sweat rate is mentioned for an embodiment of the present invention. The present invention may include all known variations of biosensors, and the description herein shows sensors as simple individual elements. It is understood that many sensors require two or more electrodes, reference electrodes, or additional supporting technology or features which are not captured in the description herein. Sensors are preferably electrical in nature such as ion-selective, potentiometric, amperometric, and impedance (faradaic and non-faradaic), but may also include optical, chemical, mechanical, or other known biosensing mechanisms. Sensors can allow for continuous monitoring of multiple physiological conditions realizing larger arrays of biomarker-specific sensors. The larger arrays can determine physiological condition through semi-specific but distinct sensors by statistical determination, eliminating the need to quantify individual biomarker levels. Sensors can be in duplicate, triplicate, or more, to provide improved data and readings. Many of these auxiliary features of the device may, or may not, also require aspects of the present invention.

Figure 2A:
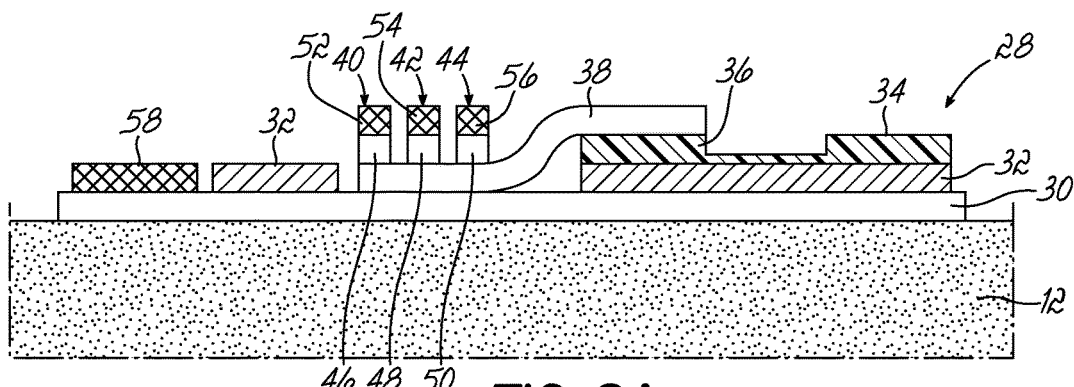
FIG. 2A is a side view diagram sweat sensor device with multiple sweat stimulation pads.

With reference to FIG. 2A, one embodiment of the present invention is designed for prolonged and reliable sweat stimulation and sensing. Arrayed stimulation pads can provide the same net effect as one pad for prolonged stimulation (e.g. one long pad for 12 hours of stimulation can be replaced by an array of 24 pads on the same device of 30 minutes stimulation each). As shown in FIG. 2A, a sweat sensor 28 positioned on skin 12 by an adhesive layer 30 bonded to fluid impermeable substrate 32. Substrate 32 holds electronics 34, one or more sensors 36 (one shown), a microfluidic component 38, coupled to multiple sweat pads 40, 42 and 44. The microfluidic component 38 can continuously pump sweat by evaporating sweat (water) from its exposed surface above sensor 36, or can include an additional continuous pumping mechanism (not shown) such as addition of a dry hydrogel capable of absorbing or wicking sweat for an extended period of time. As sweat generates its own pressure, microfluidic component 38 could also be a simple polymer microchannel, at least partially enclosed, which is pressure driven. Each pad has a source of sweat stimulant such as pilocarpine 46, 48, 50, and independently controlled iontophoresis electrodes 52, 54, 56. There is also one or more counter electrodes 58. To minimize dead volume, these pads 40, 42 and 44 are preferably less than 1 cm$^2$, for example, less than 5 mm$^2$ down to about 1 mm$^2$.

The electronics 34 further include a timing circuit connected to each electrode 52, 54, 56 via lines 66, 68 and 70 to promote sweat when desired. Thus, in operation, the electronics 34 would activate one of electrodes 52, 54 or 56 for a defined period of time. This will cause generation of sweat, which will be transferred through the microfluidic structure 38, directed to the sensor 36. After a defined period of time, the electronics 34 will discontinue current to electrode 56 and direct it to electrode 54, again causing sweat generation beneath electrode 54, but not beneath electrode 56. Again, after a period of time, the electronics 34 will discontinue current to electrode 54 and begin passing current to electrode 52, again starting sweat generation beneath electrode 52 and discontinuing sweat generation beneath electrode 54. Each one of these will direct the sweat through the common microfluidic component 38 to the sensor 36, thus providing long-term generation of sweat without stressing any particular location on the skin 12 of the individual.

Figure 3:
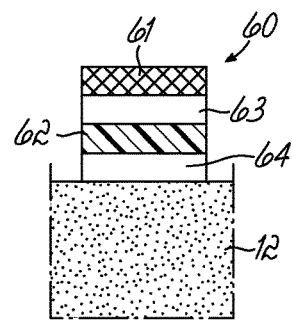
FIGS. 3-7 show one of an alternate arrangement for a plurality of arrangements for sweat stimulation, sweat collection, and sensors.

The sweat pad 60 shown in FIG. 3 represents the case where each pad 60 would have its own sensor 62 and microfluidic component 64, along with the electrode 61 and pilocarpine source 63. A plurality of these would be connected to a common circuit which would activate each pad according to a selected schedule.

In one embodiment, sensors could sense biomarkers of the effects and extent of tissue damage at a longer sweat sampling interval than sensors that could sense biomarkers of short term stress or trauma on the body, the trauma sensors having locally higher sweat stimulation than the tissue damage sensors. A higher stimulation would result in a higher sweat rate, and therefore a faster refilling of any dead volume or microfluidic volumes between the skin and sensors, and therefore an effectively shorter sampling interval. Such stimulation could also occur at regular or irregular intervals, as needed for different biomarkers.

Figure 4:
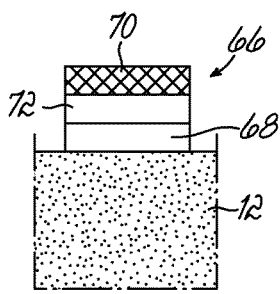
Figure 5:
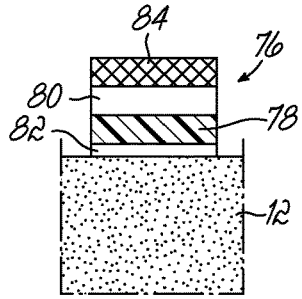
Figure 6:
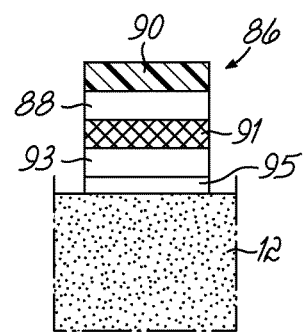

FIGS. 4-6 show different potential configurations of sweat pads, each suitable for use in the present invention.

Figure 2B:
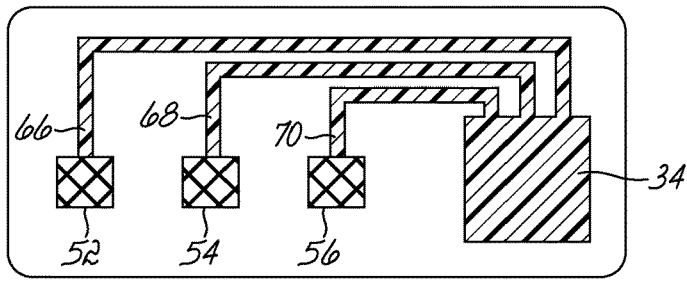
FIG. 2B is an overhead view of FIG. 2A, with only circuitry and electrodes shown.

FIG. 4 shows one of an alternate arrangement of a sweat stimulation and collection pad 66. The source 46 and the adhesive 30 of FIG. 2 is replaced with a single layer 68, which includes the adhesive, such as a hydrogel based adhesive that contains pilocarpine or other sweat stimulant. This electrode 70 activates the pilocarpine in layer 68, causing sweat generation. The sweat, in turn, flows through microfluidic layer 72 to a sensor (not shown).

FIG. 5 shows one of an alternate arrangement for a sweat stimulation and collection pads 76. The sensor 78 is immediately adjacent to the skin 12 and therefore eliminated the need for the functionality of a microfluidic component such as microfluidic element 64. For example, the sensor 78 of FIG. 5 could be fabricated on a plastic film substrate and perforated with holes (not shown) that allow for pilocarpine from source 80 to be iontophoretically dosed through the sensor 78 and adhesive 82 to the skin 12. In this embodiment, electrode 84, when activated, causes sweat generation, which immediately contacts sensor 78. Again, a plurality of three pads could be employed and activated by a common circuit. Adhesive 82 may not be required in all applications. For instance, the collection pad 76 could be a subcomponent of a larger device that is affixed to skin and therefore collection pad 76 is held in adequate proximity with skin, or a band or strap or other mechanism employed to hold collection pad 76 against skin.

FIG. 6 shows another alternate arrangement for a sweat stimulation and collection pad 86. The pad 86 includes a gate 88 and a sensor 90. The gate 88 is a structure that starts or stops fluid flow and can be a water soluble member which acts as a sweat barrier until sufficient sweat is generated to dissolve the gate to allow fluid flow. Or it can be a water soluble, water permeable member that initially promotes fluid flow and stops fluid flow after a certain amount of sweat has passed. Therefore the gate 88 can open fluid transport of sweat to the sensor 90 only at a time when desired, typically only when sweat stimulation is applied for that pad and sweat flow is robust enough that the local sweat sample is fresh and representative of a good chronological sampling of solutes in sweat. Gate 88 could also be pressure actuated by sweat itself, or activated by means such as electrowetting, thermocapillarity, or any other suitable means. Gate 88 could be reversible, for example, it could open, close, open, and close again. Pad 86 further includes a porous electrode 91, pilocarpine source 93 and adhesive layer 95. This is particularly useful for single-use sensors such as those that are easily disrupted by surface fouling with time or those with such a strong affinity for the biomarker to be detected that they are unable to detect later decreases of the biomarker concentration. Again, for such single use sensors the gating could be a physical gating of a microfluidic component carrying the sweat, or simply the sensors activated as sweat is stimulated in a manner adequate to bring sweat to the sensor. With further reference to FIG. 6 and in combination with other embodiments of the present invention, a device could also consist only of pad for sweat stimulation and with gates which couple sweat stimulation and sweat collection with one or more microfluidic components. For example, one sensor could be fed by multiple microfluidic components which stimulate sweat and collect it as needed. The gates could allow flow of fresh/stimulated sweat while blocking unstimulated sweat. The gates could also not be needed, just allowing sweat to flow freely to the sensor as it is generated by one or more stimulation pads.

Figure 7:
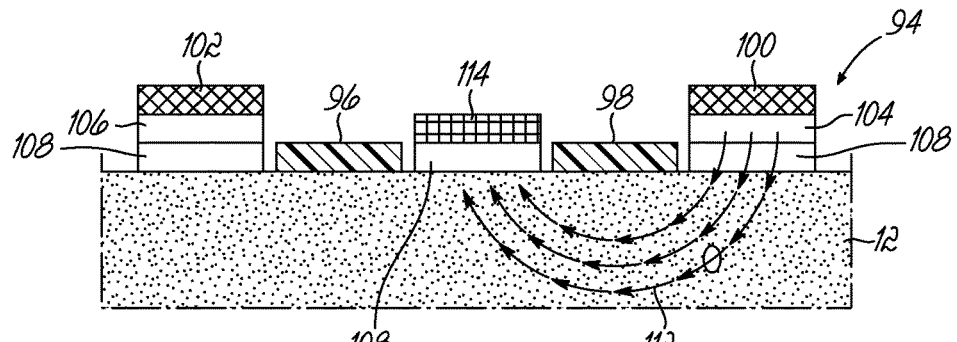

FIG. 7 is a diagram of a portion of components of a device 94, affixed to skin 12 by adhesive 108, similar to device 10 of FIG. 2 arranged in a manner that provides significantly different function and a unique manner of separation of stimulation and collection/sensing components. In some cases such as sensing ion concentrations, pilocarpine and/or other solutes or solvents or an electric field used for its delivery or purposes could alter the readings of the sensors 96, 98. Therefore the stimulation electrodes 100, 102, their respective sweat stimulations sources with pilocarpine 104, 106, and adhesives 108 are located near but spaced from sensors 96 and 98, as well as any collection pad, if used. The pilocarpine stimulation, if performed by iontophoresis, follows electrical field, a pathway indicated by arrows 112. This can result in stimulation of sweat while not bringing sensors 96 and 98 into concentrated contact with pilocarpine or other chemical sweat stimulant, or if desired reducing electric field or current on or near sensors 96 and 98. In the example embodiment shown in FIG. 7, the sensor 98 will receive significant sweat because the stimulation is occurring beneath as caused by electric field and iontophoretic current applied between electrodes 100 and ground electrode 114. Again, each of the sweat stimulation pads are preferably attached to timing circuitry that permits selective activation and deactivation of each pad.

Figure 8:
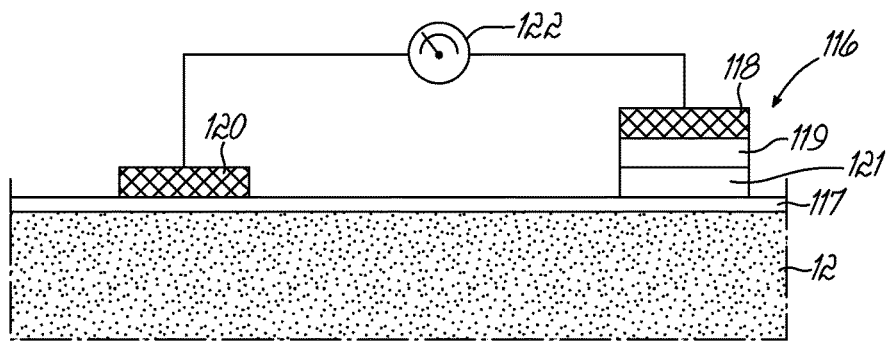
FIG. 8 shows an embodiment of the present invention that is able to detect an unreliable contact of a sweat stimulation pad with the skin.

FIG. 8 is applicable to any of the devices of FIGS. 2-7 or other embodiments of the present invention. If stimulation electrode/pad contact to the skin is inadequate, this can be detected as an increase in impedance and that pad can be deactivated for purpose of skin safety and/or inadequate stimulation. The sweat sensing device 116 affixed to skin 12 by adhesive 117, as shown in FIG. 8, senses impedance of the contact of the electrode 118 (with pilocarpine source 119 and microfluidic component 121) with the skin 12 and/or the contact of counter electrode 120 with the skin 12 where 'contact' refers to direct contact or indirect contact but which has adequate and/or uniform electrical conduction with the skin. Inadequate contact can cause insufficient sweat stimulation, an increase in current density and additionally therefore cause irritation, damage, burns, or other undesirable effects with the skin or with the function of the device. Measurement of electrical impedance includes obvious related measures such as capacitance, voltage, or current which also give a measure of impedance. If the impedance exceeds a preset limit by circuit 122, the electrode 118 can be deactivated. This reduces the likelihood of burning the skin. Furthermore, if sweat stimulation pads are redundant (one or more), the embodiment illustrated in FIG. 7 can allow the present invention to select the 'adequate' or 'best' ones for use with one or more embodiments of the present invention. In an alternate embodiment of the present invention, inadequate stimulation can also be measured by one or more known means of measuring sweat rate, such as impedances, lactate concentration, or sodium or chloride concentration.

In an alternate embodiment, each counter electrode and iontophoresis electrode of the embodiments of the present invention can be placed close to each other and/or controlled in conjunction with each other. To allow prolonged sweat stimulation but to limit areas of skin to shorter term stimulation, each sweat stimulant source and electrode could be utilized sequentially. For example, if a safe protocol for stimulation was found to be up to 1 hour, but 24 hours of stimulation and sensing is needed, then 24 sets of electrodes and sources could be used sequentially. Also, after a period of time, stimulation can be reactivated under a given electrode and source (for example, sweat generation could become 'tired' and after 'resting' for some time, be enacted again at the same time). Therefore multiple sequences or timings of stimulations and collections are possible, to enact sampling of sweat at multiple intervals or continuously for a longer period of time than is conventionally possible. Multiple microfluidic components could be associated with one-way flow valves as well, reducing fluid flow contamination or confusion between multiple fluidic pathways or elements. The time scales listed herein are examples only, and stimulation for less regular, more short, or even longer total durations are possible.

In an alternate embodiment, each stimulation pad, even if with or without a microfluidic component, can have a volume between skin and sensor such that reduced stimulation is allowed while still providing adequate chronological resolution (sampling interval). Conventional sweat stimulation requires >1 nL/min/gland flow of sweat to allow a proper sampling volume. The present invention allows the sweat stimulation to be reduced to <2 nL/min/gland, preferably <0.5 nL/min/gland using sweat stimulation concentrations/dosages as found in the literature (e.g. Buono 1992, J. Derm. Sci. 4, 33-37) appropriate for such reduce stimulation and sweat rates. Such an alternate embodiment can be desirable, because it can reduce one or more of the undesirable aspects or side-effects of sweat stimulation or prolonged sweat stimulation. Enabling calculations for reduced stimulation, sweat rates, volumes and areas, were provided in the background section.

For sensors located on the palms or soles the skin is very thick and if becomes wet for prolonged periods of time the sweat can slow unacceptably or stop altogether as skin swells to the point where sweat ducts become pinched off. Such state is visibly noticeable as 'wrinkling of the skin' after the skin is exposed to water for a longer period of time. Therefore for prolonged sensing, a dessicant, hydrogel, or other absorbent material can be placed over top or adjacent to the sensors of the present invention to enable longer term viability of sensing of the palm or sole with reduced concern of skin swelling/wrinkling and reduced sweat flow rate either natural or stimulated.

Figure 9A:
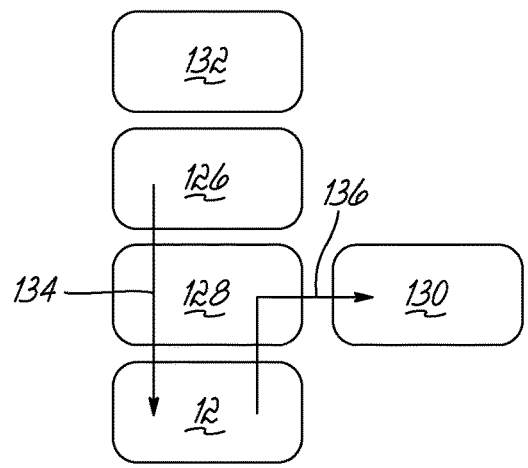
FIGS. 9A and 10A are block diagrams of the functionality of integrated sweat stimulation and sweat sampling.
Figure 9B:
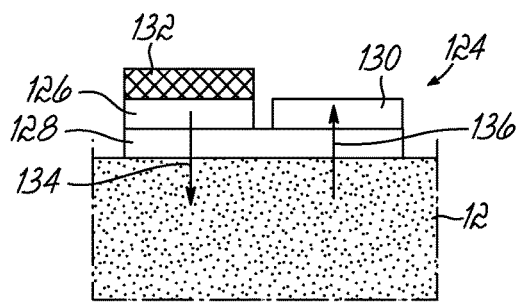
FIGS. 9B and 10B are cross-sectional representations of the embodiments shown in FIGS. 9A and 10A.
Figure 10A:
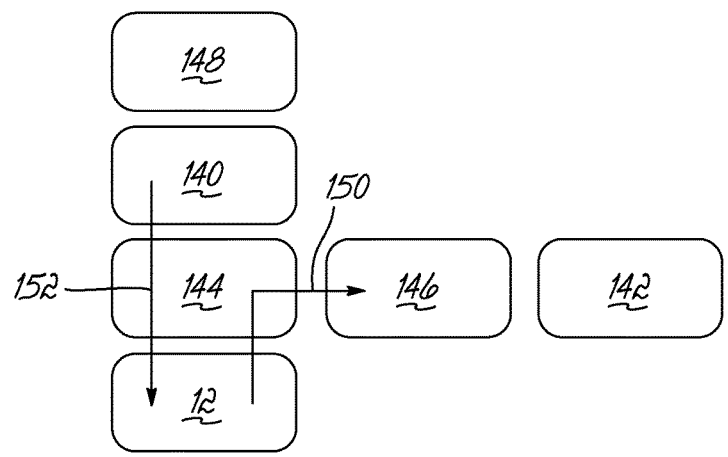
Figure 10B:
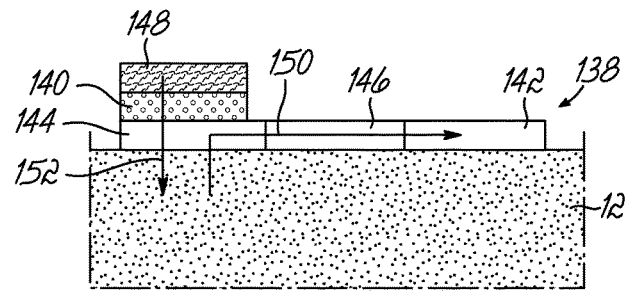

With reference to FIGS. 9 and 10, an alternate embodiment of the present invention is shown using block diagrams to convey function of a more advanced example subset of components of devices of the present invention. The components shown for the device 124 in FIG. 9 has a pilocarpine source reservoir 126 which contains a sweat stimulating compound such as pilocarpine, a fluidic component 128, and a sampling component 130, all of which are integrated in a device resting on skin 12. Fluidic component 128 and sampling component 130 could also be one and the same where sampling component 130 is just an extension of the fluidic component 128. In an example embodiment, an electrode 132 is provided to reservoir 126, thus enabling iontophoretic dosing of pilocarpine through fluidic component 128 and into skin 12 as indicated by arrow 134. This dosing of pilocarpine generates sweat, which is initially wetted into fluidic component 128 and then transported into sampling component 130 as indicated by arrow 136. The sweat may travel along a partially separate flow path than the pilocarpine to minimize interaction between the sweat and the pilocarpine, but full separation is not required. The above example could be achieved by using pilocarpine placed into a hydrogel which forms the reservoir 126, stacked onto a thin piece of paper or other fluid porous material for the fluidic component 128, which is then connected to another piece of paper or tube for the sampling component 130. The sampling component 130, or even fluidic component 128, may contain or be in fluidic contact one more sensors (not shown), or may simply store sweat for later analysis by a sensor external to the device 124. In further examples, the iontophoresis could be continuous, and allow continuous sampling of non-charged biomarkers or solutes in sweat, or the iontophoresis could be intermittent and between dosing by iontophoresis both charged and non-charged biomarkers or solutes in sweat could be sampled.

Components 126 and 128 in alternate designs could also be one and the same, as could also be true for components 128 and 130. To minimize sweat solute diffusion into or out of the reservoir 126, the reservoir 126 may be made of a material such as a gel that is slow to diffusion of solutes but fast in allowing iontophoretic transport of solutes. A non-limiting example would be an ion-selective membrane with selectivity partial to pilocarpine or substances with charge or makeup similar to pilocarpine.

FIG. 10 shows a sweat sensing device 138 with similar features as FIG. 9, but also includes a membrane 140 and a storage component 142. The storage component 142 may simply collect and store sweat as it is sampled through the sampling component 146. The storage component 142, could for example, be a hydrogel which swells and increases in volume as it takes up a fluid like sweat. The sampling component 146 can include one more sensors providing a chronological measure of biomarker concentration in sweat instead of a time-integrated measure that would occur if the sensor were instead placed in the storage component 142. Sensors could also be placed at or near the location of fluidic component 144, or at or near the skin 12, as described for previous embodiments of the present invention. The membrane 140 is any component that allows pilocarpine or other compound diffusion or iontophoresis through the membrane 140, but which reduces or prevents diffusion of biomarkers or solutes in sweat through the membrane 140 and back into the pilocarpine reservoir 148. Furthermore, membrane 140 can serve as a barrier to fluidic contact between reservoir 148 and other components of the device 138 of the present invention to increase storage life as pilocarpine gels typically are hydrated and can diffuse out pilocarpine over time into other porous media they are brought into contact with. Reservoir 148 and membrane 140 could also be one and the same, with membrane having selective transport for sweat stimulating substance. For example, selective membranes or materials that are partial to transport sweat stimulant can be known membranes partial to transport of only one type of ion polarity (for example for favoring the charge of the sweat stimulant ions) or partial transport to molecules as small as but not substantially larger than the sweat stimulation molecule through simple principles of size exclusion. Further examples can be found through literature on 'selective molecular sieves'.

As a result, sweat stimulation and sampling can be integrated in the same device with less interference between the two. For example, the membrane 140 could be a track-etch membrane with 3% porous open area, and the pilocarpine concentration and iontophoretic driving voltage increased on the reservoir 148 such that the amount of pilocarpine dosed can be similar or equal in effectiveness to that that of a reservoir 148 placed directly against the skin 12. Because the membrane 140 only has 3% porous area, diffusion of solutes in sweat into the reservoir 148 is reduced substantially up to 30×. The fluidic component 144 may be adequately thick that any pilocarpine coming through holes or pores in the membrane 140 would have adequate distance before reaching the skin to spread out into a more even concentration and current density into the skin. Membrane 140 could be any material, film, ion-selective gel, or other component which transports a sweat stimulating component such as pilocarpine, but which minimizes the transport of other all or particular sweat solutes back into the reservoir 148. Membrane 140 therefore could also be a fluidic or ionic switch or valve, which is opened during a short period of time for iontophoresis of pilocarpine, but closed once an adequate pilocarpine dose has been released from the reservoir 148. Furthermore, membrane 140 can serve as a barrier to fluidic contact between reservoir 148 and other components of the devices of the present invention to increase storage life as pilocarpine gels typically are hydrated and can diffuse out pilocarpine over time into other porous media they are brought into contact with. For cases where the membrane 140 is a fluidic switch an electrode may be provided with the fluidic component 144 to complete iontophoresis of pilocarpine even after the fluidic switch 140 is closed to pilocarpine transport. Example fluid switches include those actuated by electrowetting, switchable selective ion channels, and other means achieving the same desired functionality.

In an alternate embodiment of the present invention, with further reference to FIG. 10, reservoir 148 will include an electrode to drive electrophoresis (not shown), and the electrode may also be utilized to measure sweat rate by electrical impedance with skin 12. In one example embodiment, to allow proper measurement of sweat rate by impedance, the electrical impedance of membrane 140 should be similar to or preferably less than the electrical impedance of skin 12 (these two impedances being in series, such that skin impedance dominates and improves the quality of sweat rate measurement by impedance). Using first principles, this is easily achieved assuming electrical conductivity of fluids in the device 138 to be roughly equal, and the sum of the electrical resistance of pores in membrane 140 to be less than the sum of the electrical resistance due to sweat ducts in skin 12. Therefore, membrane 140 could be selected such that it has a low enough porosity to help prevent contamination between reservoir 148 and fluidic component 144, but also having high enough porosity such that it does not block proper impedance measurement of skin 12. Fortunately, impedance can be measured using a small signal AC waveform, which results in little or no net migration of pilocarpine or other charged sweat stimulant.

In an alternate embodiment of the present invention, with further reference to FIGS. 9 and 10 the reservoir of pilocarpine and fluidic component can also be switched in locations (trading locations as illustrated and described, but retaining their primary functionalities and the advantages/features as described for embodiments of the present invention).

For the embodiments of FIGS. 9 and 10, it is desirable for some applications that the fluid capacity, or volume, of the fluidic and sampling components 144 and 146 be as small as possible. This is important, because if the fluidic and sampling components 144 and 146 have a large volume, the components will effectively integrate the concentrations of solutes in sweat over a longer period of time, and limit the ability to achieve a time-resolved measurement of solutes in sweat. Furthermore, any delay on transporting sweat from the skin 12 to a sensor can cause degradation in concentrations of some biomarkers or solutes in sweat, and therefore minimum volume of the fluidic and sampling components 144 and 146 is also desirable.

Figure 11:
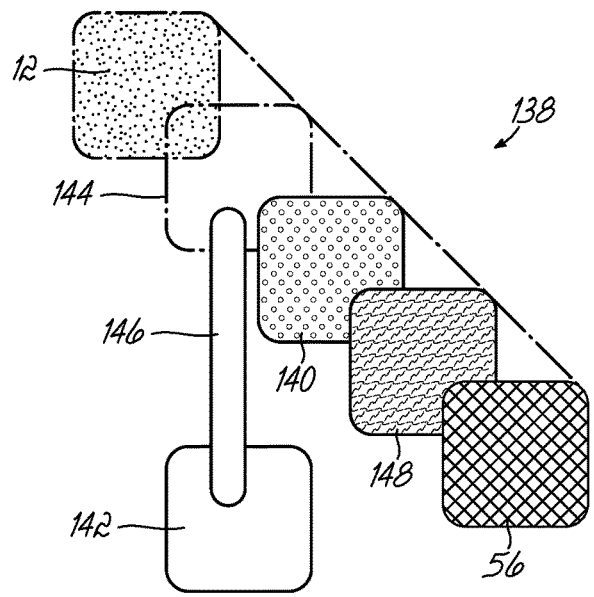
FIG. 11 is a diagrammatic top plan view of the layers used in the device shown in FIG. 10A.

An example stack-up of an embodiment of the components comprising the device 138 is shown in FIG. 11. As represented by arrow 150 of FIG. 10, sweat will flow along sampling component 146 to storage component 142 while pilocarpine flows directly to the skin 12 as shown by arrow 152.

Sweat stimulation can be applied continuously or repeatedly over long periods of time so long as the currents utilized for iontophoresis and total doses are properly controlled. In yet another embodiment of the present invention devices can include controllers which allow sweat stimulation for periods of hours to potentially more than a day in duration.

In some cases, even with careful electrical controllers and microfluidic design, skin irritation could occur, and in these cases in yet another alternate embodiment of the present invention includes sweat stimulation pads that are <50 mm$^2$ in order to reduce perceived irritation by the user, even less than 10 mm$^2$ or less than 2 mm$^2$. These ranges for the present invention are much smaller than the commercial Wescor product, which has a stimulation pad that is >1 cm$^2$ (>100 mm$^2$), because large amount of sweat needs to be collected given the highly manual nature of the sweat collection and sensing. Assuming ~100 sweat glands/cm$^2$, a 50 mm$^2$ stimulation pad could collect sweat from on average 50 glands, 10 mm$^2$ on average 10 glands. If the stimulation pad is placed in regions where sweat gland density is >350 glands/cm$^2$ then a 2 mm$^2$ stimulation pad could cover on average >6 glands and most likely at least one gland always with careful placement. The present invention may also use much larger sweat stimulation pads, if it is acceptable for the application and/or other embodiments of the present invention are utilized to suitably reduce irritation caused by sweat stimulation.

In some cases, even with careful electrical controllers, reduced stimulation area, and advanced microfluidic design, skin irritation could occur, and in these cases in yet another alternate embodiment of the present invention, the pilocarpine reservoir can also contain an iontophoretically transported or diffusing anti-inflammatory, numbing agent, or pain-relieving agent (hydrocortisone, for example, or other iontophoretically delivered pain relieving agents). This could allow longer stimulation and usage than otherwise deemed acceptable by the user. Ideally, the anti-inflammatory or pain relieving/numbing agent delivered will have properties such as: (1) not interfering with sweat stimulation (not suppressing it); (2) have a similar charge polarity as the sweat stimulating substance and be co-delivered to the same site with it. For example, deliver combinations of stimulant or anti-inflammatory/numbing agents, such as "name (example charge polarity)": (1) stimulants—Pilocarpine (+), Acetylcholine (+), Methacholine (+), Phenylephrine Hydrochloride (+), Isoproterenol (+); (2) anti-inflammatories/numbing agents—such as Dexamethasone (−), Hydrocortisone (+ or − depending on compound), Salicylate (−), Lidocaine. Several of such substances or molecules can also be altered in charge to work with positive or negative polarity. Furthermore, even oppositely charged substances could be co-delivered to the same location as sweat extraction takes place, for exampling, using an electrode arrangement using features similar to that shown in FIG. 7 where the numbing agent would be delivered using electrodes that are side by side with electrodes delivering sweat stimulant, and in between such electrode pairs sweat would be collected. Furthermore, agents to reduce pain or irritation or swelling could be allowed to penetrate by diffusion over time (charged or uncharged), as some agents such as hydrocortisone work well based on diffusion alone and do not need to penetrate overly deeply into the skin. Numerous such combinations are possible, the key requirement being delivery either simultaneously or at other times which allow both sweat stimulation and chemical or pharmalogical reduction of irritation, pain, or inflammation. An excellent reference, included herein, is Coston and Li, Iontophoresis: Modeling, Methodology, and Evaluation, *Cardiovascular Engineering: An International Journal*, Vol. 1, No. 3, September 2001 (C ° 2002).

The reservoir may also contain a surfactant or other substance that can cause cell death, cell rupture, or increase skin cell membrane permeability, in order to facilitate biomarker release from the body into the sweat being sampled. The reservoir may also contain solvents known to increase the effectiveness of iontophoretic delivery. Furthermore, techniques such as electro-osmosis can be used continuously or intermittently to promote extraction of biomarkers from the cells surrounding a sweat duct or from the skin directly. Also, for long duration sweat stimulation, the iontophoresis could potentially cause electrolysis of water and therefore high concentrations of acids or bases at the two or more electrodes required for iontophoresis. Therefore in yet another alternate embodiment of the present invention, the electrodes contacting components, such as that contacting the reservoir or electrode, may also be equipped with buffering agents, or the electrodes themselves undergo oxidation or reduction in order to suppress undesirable side-effects of water electrolysis and/or pH changes.

With further reference to the example embodiments of the present invention, sweat generation rate could also be actively controlled to decrease, by iontophoresis of a drug which reduces sweating, such as anticholingerics including glycopyrrolate, oxybutynin, benztropine, propantheline. For example, a sweat retarding chemical could replace pilocarpine in reservoir 126 of FIG. 9A. Sweat generation rate could also be reduced by administering a solvent to the skin such as glycols which can swell the top layer of skin and pinch off the sweat ducts such that sweat generation rate is reduced by constriction of flow of sweat to the surface of skin. Other antiperspirant compounds or formulations, such as Aluminum chloride are possible as well. Why would one want to slow the sweat generation rate? Two non-limiting examples include the following. Firstly, some sensors or subcomponents could foul or degrade in performance more quickly as fresh sweat is brought to them, or the general maximum usage time of the patch decrease as a result of a sweat generation rate that is too high. Second, some solutes or properties of sweat could be read more reliably at lower sweat generation rates, in particular low concentration solutes could have more time to diffuse into slowly flowing sweat inside the sweat gland/duct and therefore a lower sweat generation rate could produce a higher concentration which could be more easily sensed by a sensor. Furthermore, some solutes are generated by the sweat gland itself during high levels of sweat generation (such as lactate) and could interfere with sensors for other solutes or sensors trying to sense lactate diffusing into sweat from blood.

This has been a description of the present invention along with a preferred method of practicing the present invention, however the invention itself should only be defined by the appended claims.

What is claimed is:

1. An apparatus to measure or collect sweat over an extended period of time, comprising:
   a plurality of sweat stimulation pads, wherein each sweat stimulation pad includes: a sweat stimulant, an electrode, and a sweat stimulant carrying medium, and wherein the pad is adapted to deliver the sweat stimulant to skin to generate sweat;
   one or more sweat collectors;
   one or more sensors for measuring a characteristic of an analyte in sweat, wherein the sensor is in fluidic communication with the sweat collector; and
   a timing circuit adapted to selectively activate and deactivate said plurality of sweat stimulation pad for one or more limited periods of time, wherein each sweat stimulation pad is selectively operable by said timing circuit.

2. The apparatus of claim 1 wherein at least two pads have different sweat stimulation rates.

3. The apparatus of claim 1 wherein each of said pads includes a sweat flow path leading to a sensor.

4. The apparatus of claim 3 wherein each sweat flow path leads to the same sensor.

5. The apparatus of claim 3 wherein each flow path leads to a separate sensor.

6. The apparatus of claim 3 wherein at least one flow path includes a gate selectively operable to allow sweat flow only during a selected time.

7. The apparatus of claim 1, further comprising an electrical sensor associated with each sweat stimulation pad, said sensor adapted to detect direct or indirect contact between said pad and skin, which permits deactivation of said pad.

8. The apparatus of claim 7 wherein said electrical sensor detects impedance.

9. The apparatus of claim 1, further comprising at least one sensor which receives sweat resulting from stimulation by said stimulation pad wherein said sensor and said stimulation pad are not fluidically coupled.

10. The apparatus of claim 1 wherein at least one sweat stimulation pad of the plurality of sweat stimulations pads is configured to stimulate an area of less than 50 mm$^2$ to reduce irritation perceived by the user of the apparatus.

11. The apparatus of claim 1 wherein at least one sweat stimulation pad of the plurality of sweat stimulations pads is configured to stimulate an area of less than 10 mm$^2$ to reduce irritation perceived by the user of the apparatus.

12. The apparatus of claim 1 wherein at least one sweat stimulation pad of the plurality of sweat stimulations pads is configured to stimulate an area of less than 2 mm$^2$ to reduce irritation perceived by the user of the apparatus.

13. The apparatus of claim 1 wherein each of said collection pads includes a gate operable to prevent flow of sweat to a sensor.

\* \* \* \* \*